(12) United States Patent
Laster

(10) Patent No.: US 10,528,911 B1
(45) Date of Patent: Jan. 7, 2020

(54) MEDICATION IDENTIFICATION AND INVENTORY CONTROL SYSTEM

(71) Applicant: Bobby J. Laster, El Sinore, CA (US)

(72) Inventor: Bobby J. Laster, El Sinore, CA (US)

( * ) Notice: Subject to any disclaimer, the term of this patent is extended or adjusted under 35 U.S.C. 154(b) by 0 days.

(21) Appl. No.: 16/545,500

(22) Filed: Aug. 20, 2019

Related U.S. Application Data

(60) Provisional application No. 62/721,167, filed on Aug. 22, 2018.

(51) Int. Cl.
*G06Q 10/08* (2012.01)
*G16H 20/10* (2018.01)

(52) U.S. Cl.
CPC ......... *G06Q 10/0875* (2013.01); *G16H 20/10* (2018.01)

(58) Field of Classification Search
CPC ............................ G06Q 10/0875; G16H 20/10
See application file for complete search history.

(56) References Cited

U.S. PATENT DOCUMENTS

2017/0302880 A1* 10/2017 Cizerle ................. H04N 5/772
2018/0247703 A1* 8/2018 D'Amato ............ G06F 19/3462

OTHER PUBLICATIONS

Bobby Laster, Blaster Communications Inc Product Video, May 18, 2016, YouTube Video, https://www.youtube.com/watch?v=Hk0mOSbHcYQ&feature=emb_logo (3 screenshots attached) (Year: 2016).*

* cited by examiner

*Primary Examiner* — A. Hunter Wilder
(74) *Attorney, Agent, or Firm* — Chen Huang; Adli Law Group P.C.

(57) ABSTRACT

A system and a method for medication identification and inventory control is disclosed. The disclosed system and method were designed to track specified medications' (e.g., narcotics and controlled substances) inventory from manufacturer's lot number all the way to the use/waste stage of the medications and to provide periodic reports and notifications on the medications' usage, breakage, waste and expiration. Further, the disclosed system and method utilizes tamper evident bags with unique identifier to protect and keep accurate track of the medications.

17 Claims, 12 Drawing Sheets

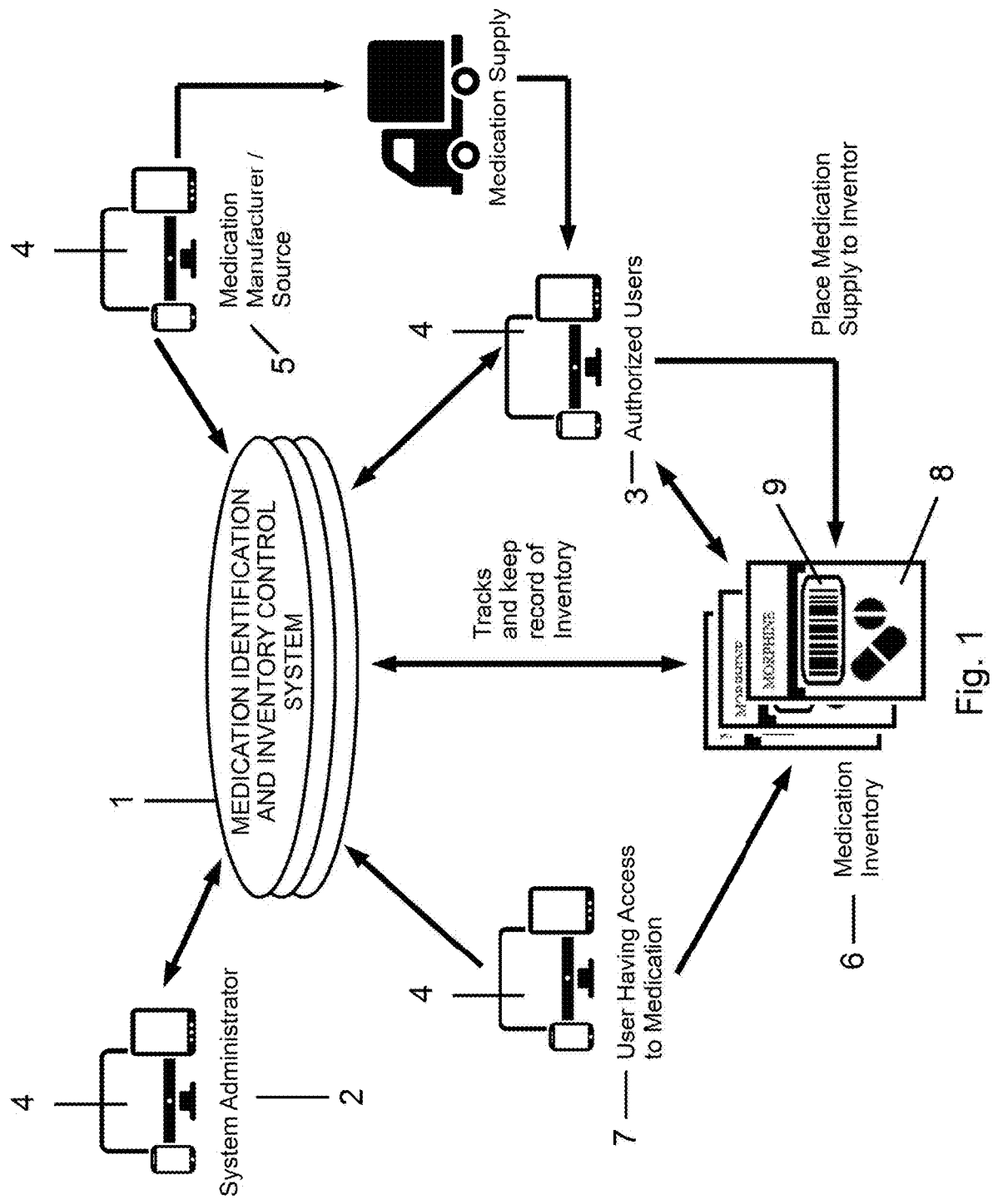

Back | Add

Morphine Current Count: 3
Max Count Allowed: 15

Versed Current Count: 4
Max Count Allowed: 5

Fentanyl Current Count: 6
Max Count Allowed: 7

Valium Current Count: 1
Max Count Allowed: 5

Back — 4

Drug Name:

Enter the mg/mcg for one drug:
(one of the drugs has this mg amount)

Inventory Min Amount (mg/mcg):
(allowed for Paramedics or ALS Units)

Inventory Max Amount (mg/mcg):
(allowed for Paramedics or ALS Units)

Min Drug Count:
(Inventory min divided by one drug amount)

Max Drug Count:
(Inventory max divided by one drug amount)

Drug Current Count:
(number of drugs assigned to bags)

Fig. 2

Drug Name: Morphine

Enter the mg/mcg for one drug: 4mg
(one of the drugs has this mg amount)

Inventory Min Amount (mg/mcg): 32mg
(allowed for Paramedics or ALS Units)

Inventory Max Amount (mg/mcg): 60mg
(allowed for Paramedics or ALS Units)

Min Drug Count: 8
(Inventory min divided by one drug amount)

Max Drug Count: 15
(Inventory max divided by one drug amount)

Drug Current Count: 3
(number of drugs assigned to bags)

Fig. 3

MEDICATION IDENTIFICATION AND INVENTORY CONTROL SYSTEM

CROSS-REFERENCE TO RELATED PATENT APPLICATIONS

Embodiments of the present invention relate to U.S. Provisional Application Ser. No. 62/721,167, filed Aug. 22, 2018, entitled "MEDICATION IDENTIFICATION AND INVENTORY CONTROL SYSTEM", the contents of which are incorporated by reference herein in its entirety and which is a basis for a claim of priority.

FIELD OF THE INVENTION

Embodiments of the present disclosure generally relate to a medication identification and inventory control system and more specifically to an inventory control system that accurately tracks specified medication inventory from manufacturer to its usage and provides periodic report on the usage, breakage, waste and expiration of the medication to system administrator and/or users.

BACKGROUND OF THE INVENTION

The incidence of drug abuse has been increasing at an alarming rate over the past decades. For examples, according to National Institute on Drug Abuse, more than 130 people in the United States die every day after overdosing on opioids. The misuse of and addiction to opioids—including prescription pain relievers, heroin, and synthetic opioids such as fentanyl—is a serious national crisis that affects public health as well as social and economic welfare. The Centers for Disease Control and Prevention estimates that the total "economic burden" of prescription opioid misuse alone in the United States is $78.5 billion a year, including the costs of healthcare, lost productivity, addiction treatment, and criminal justice involvement. Further, opioids are not the only controlled substances that are prong to addiction and abuse. Many other controlled substances have also been found to be addictive.

According to a study and statistic, in 2018, more than 47 million doses of legally prescribed opioids were stolen, which is an increase of 126 percent from the year before. The study also found 34 percent of these incidents happened at hospitals or medical centers, followed by private practices, long-term care facilities and pharmacies. Only 77 percent of the cases identified a particular drug, but the most common was Oxycodone, followed by hydrocodone and fentanyl. As it can be seen, drug theft and diversion are some major causes for the drug abuse.

The U.S. Department of Justice's Drug Enforcement Administration has established recordkeeping requirements requiring registered practitioners to keep records of controlled substances that are dispensed to the patient, other than by prescribing or administering, in the lawful course of professional practice. While practitioners are required to maintain records related to controlled substances and the records must be available for inspection for a minimum of two years, there is no requirement requiring practitioners to conduct inventory count periodically. In many incidences, it may take a while for a hospital or practitioner to discover that certain controlled substances were stolen or missing especially when many inventory counts are done in batches.

Because the drug counts may not always be accurate due to lack of periodic checks, the medical personnel may not always have accurate records of available drugs. This can lead to problems in the event of major disaster or emergency when there is a shortage of certain medicines in a hospital and the hospital needs to get them from other sources. The inaccuracy in drug counts may cause delays to the process and the rescues.

Accordingly, there exists a need for an improved system and method for medication identification and inventory control. There also exists a need for an improved system and method for assisting fire stations, hospitals, pharmacies and EMS staffs to track narcotics and prevent diversion to help manage victims after a major disaster or emergency.

SUMMARY OF THE DISCLOSURE

The major objective of the present disclosure is to provide an inventory tracking and control system for medications. The disclosed system was designed to track specified medications (e.g., narcotics and controlled substances) inventory from manufacturer's lot number all the way to the use/waste stage of the medications and to provide periodic (e.g., daily and monthly etc.) reports and notifications on the medications' usage, breakage, waste and expiration.

In accordance with one aspect of at least one embodiment of the present disclosure, the disclosed medication identification and inventory control system comprises a system server having a non-transitory computer-readable storage medium comprising programmable instructions adapted to be executed on one or more processors of the system server, and to perform a method of: receiving registration information from a system administrator; requesting the system administrator or user authorized by the system administrator to specify a list of medications to be tracked; receiving the list of medications to be tracked from the system administrator or user authorized by the system administrator; receiving information relating to medications delivered from a manufacturer whenever medications within the list of medications are delivered from the manufacture to the system administrator or to a place specified by the system administrator or by the authorized user, wherein the information relating to medications includes at least the quantity and expiration date of the medications delivered; receiving delivery confirmation from the system administrator or the authorized user, wherein the delivery confirmation confirms at least the quantity of the medications received matches the quantity of the medications delivered; instructing the system administrator and any user authorized to have access to the list of medications to report medication usage through their computing or mobile device whenever a medication within the list of medications is used or wasted; receiving information relating to the medication's usage from the system administrator and the user authorized to have access to the list of medications' through their computing or mobile device and storing information relating to the medication's usage in a database; and periodically generating and delivering a medication inventory report or upon request by the system administrator or authorized user for medications within the list of medications, wherein the medication inventory report comprises at least medications within the list of medications' usage, breakage, waste and expiration.

Among other things, the disclosed system is designed to help Fire Stations, Hospitals, Pharmacies and EMS staffs to accurately track and maintain their medication inventory, particularly the quantity, usage and expiration date of controlled medications, substances and narcotics. The chain of responsibility can track the medication inventory from manufacturer's lot number all the way to the use/waste stage using standard code technology (e.g., QR code, bar code).

The system can be accessed by mobile application associated with the system through mobile devices such as iPhone, iPad and tablet computer and also accessed by desktop computer as well. All data is stored in the cloud, data-centers and/or servers and can be accessed through Wi-Fi, cellular signal, the internet or intranet from anywhere.

The foregoing and other objects, features and advantages of the present invention are more readily apparent from the detailed description of the preferred embodiments set forth below, taken in conjunction with the accompanying drawings.

BRIEF DESCRIPTION OF THE DRAWINGS

FIG. 1 is a schematic drawing according to an exemplary embodiment of the present invention.

FIG. 2 is a schematic drawing according to an exemplary embodiment of the present invention.

FIG. 3 is a schematic drawing according to an exemplary embodiment of the present invention.

DETAILED DESCRIPTION OF PREFERRED EMBODIMENTS

Figure 4:
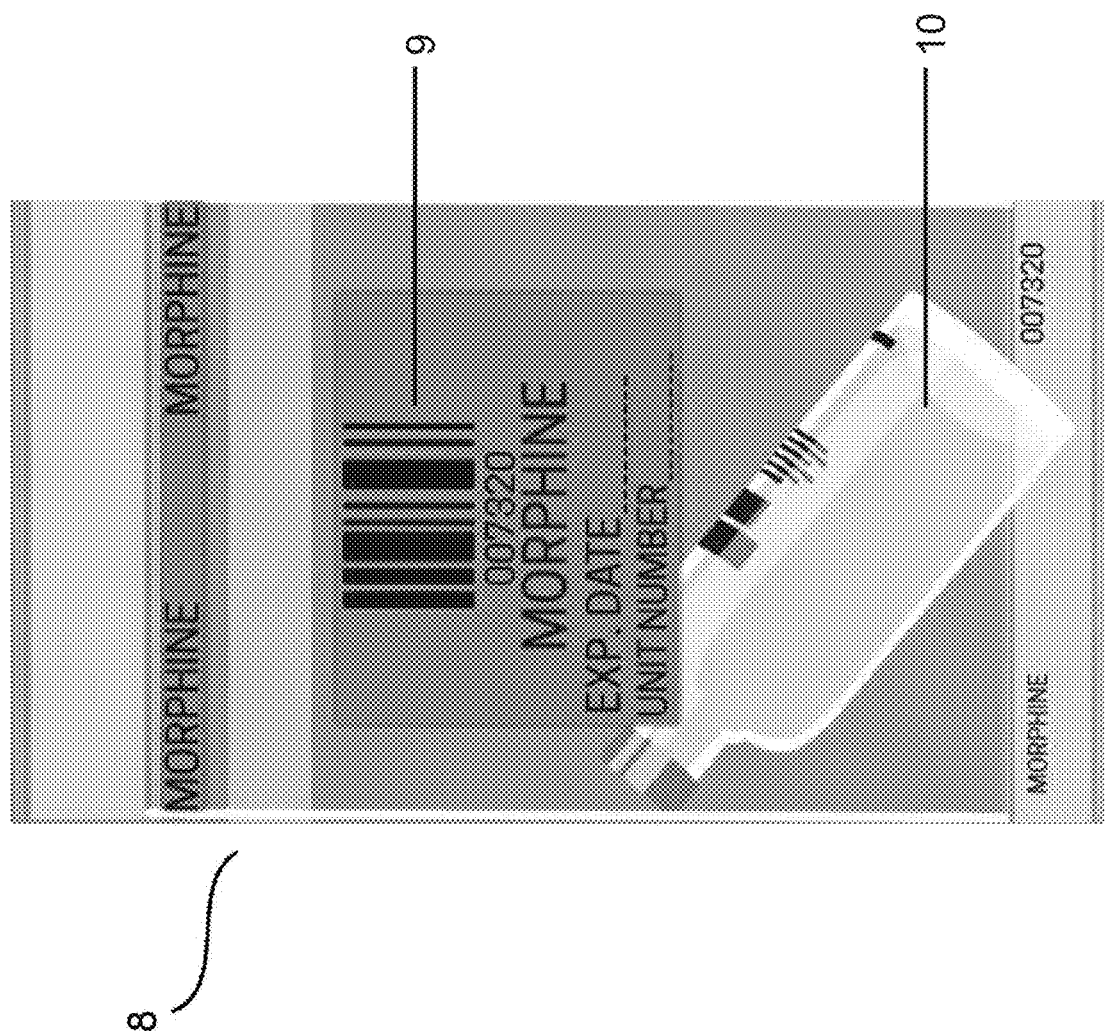
FIG. 4 is a schematic drawing according to an exemplary embodiment of the present invention.

The following description is not to be taken in a limiting sense, but is made merely for the purpose of illustrating the general principles of the invention, since the scope of the invention is best defined by the following claims. Various inventive features are described below that can each be used independently of one another or in combination with other features.

For purpose of present disclosure, the term "system administrator" generally refers to a person who has the authority to manage the operation of the disclosed medication identification and inventory control system. The system administrator is not limited to medical personnel and can be a third-party vendor. The term "authorized user" or "authorized users" generally refers to user(s) who are authorized by the system administrator to access the disclosed system while "user authorized to have access to the list of medications" refers to user(s) who has access to the medications tracked by the disclosed system. "Authorized user" may include "user authorized to have access to the list of medications" so a person can be both "authorized user" and "user authorized to have access to the list of medications" at the same time.

For purpose of present disclosure, the term "controlled substance" includes medications classified as Schedule I through V by the Federal Drug Enforcement Agency. The term "tamper evident bag" or "narcotic tamper evident bag" usually refers to a device or process that makes unauthorized access to the protected object easily detected. Seals, markings or other techniques may be tamper indicating.

Broadly, embodiments of the present disclosure generally provide a medication identification and inventory control system that accurately tracks specified medication inventory from medication manufacturer/vendor to receiving party (e.g., fire stations, hospitals, pharmacies and EMS staffs) and all the way to the use/waste stage of the medications, and provide periodic report on medication usage, breakage, waste and expiration to users and/or administrators.

In accordance with one aspect of at least one embodiment of the present disclosure, as shown by FIG. 1, the disclosed system 1 comprises: a server having a hardware processor configured to: receive registration information from a system administrator 2 and authorized users 3 (e.g., personnel working for a fire station, a hospital, a pharmacy or an emergency medical service etc.); request the system administrator 2 or authorized users 3, via their mobile devices or computers 4, to enter a list of medications (i.e., controlled substances, narcotics etc.) that are to be tracked and medications' information such as name and current inventory count of each medication available (as illustrated by FIG. 2) in their medication inventory 6; receive and store the list of medications and medications' information in a database accessible by the system 1; receive a delivery notification from the system administrator 2 or authorized users 3 when a medication within the list of medication is delivered from a manufacture or a source 5 and received by the system administrator 2 or by the authorized users 3 or at a place specified by the system administrator 2 or authorized users 3 (e.g., hospital, clinic etc.); wherein the delivery notification includes at least system administrator 2 or authorized users' 3 confirmation confirming quantity of the medication received matches the quantify of the medication delivered and optionally the expiration date of the medication; update the inventory count and expiration date of the medication in the database based on the delivery notification; receive medication usage via the system administrator 2 or authorized users' 3 mobile devices or computers 4 whenever a medication within the list of medication is used or wasted and update the medication's information in the database; notify the system administrator 2 or authorized users 3 to conduct periodic inventory count for medications in the list of medications (or medication inventory 6) through their mobile devices or computers 4; receive the periodic inventory count from the system administrator 2 or authorized users 3 via their mobile devices or computers 4 and verify whether the periodic inventory count matches the inventory count in the database of the system 1, and send alert to the system administrator 2 or authorized users 3 when a mismatch is detected; and periodically generate and deliver a medication inventory report or upon request by the system administrator 2 or authorized users 3 for medications within the list of medications, wherein the medication inventory report comprises at least medications' usage, breakage, waste and expiration.

For example, the system 1 can be configured to generate and send daily reports and notifications to system administrator 2 and authorized users 3 on medication usage, breakage, waste and expiration. All data can be stored in an on-site storage device, the cloud, data-centers and/or servers and can be accessed through Wi-Fi, cellular signal, the internet or intranet from anywhere. The system administrator 2 and/or authorized users 3 can add new medication category into or remove existing medication category from the original list of medications and modify the information therein if necessary. FIGS. 2 and 3 show an exemplary process for creating new medication category via mobile application on a mobile device 4. The mobile application provides an interface for system administrator 2 and/or authorized users 3 to enter at least the name of the new medication category and the new medication category's current inventory count. The system 1 may also be configured to allow administrator 2 and/or authorized users 3 to set maximum and/or minimum count for each medication entered. The system 1 can be configured to alert the administrator 2 and/or authorized users 3 whenever the current drug count exceeds the maximum drug count or falls below the minimum drug count. This can effectively prevent certain medication inventory from shortage or being excessive.

In one embodiment of the present disclosure, the disclosed system 1 provides an Administrator App (or Admin App) for the system administrator 2, which primarily utilizes desktop computer or tablets like iPads to access the system and provides a User App for authorized user(s) 3 and/or user(s) authorized to have access to the list of medications 7 (collectively "users"), which primarily utilizes mobile device 4 such as mobile phone to access the system 1. The system is configured in a way that the system administrator 2 is capable of assigning user IDs and passwords (e.g., the initial password) to the users (3 and 7), setting up company and vendor/manufacture 5 profiles, and creates reports on all activities. The Administrator App can also see all patients/victims' information sent by the User Apps in real time. Each authorized user 3 or user authorized will have access to the list of medications 7 logs into the User App with the assigned User ID and Password provided by the system administrator 2 to access an incident to begin assessing and administering medications to patients/victims. Optionally, Admin App and User App may also be configured to allow users to login via biometric recognitions such as facial recognition, finger print and retina recognition etc. as alternative ways to ID/Password to expedite the login process. Since biometric recognitions generally have higher level of security, the disclosed system 1 and its applications can also be configured to require users to use biometric recognition or higher level of authentication method (e.g., two or three steps verification etc.) when more sensitive medications and narcotics are being handled or administered. Also, information relating to medications delivered from the manufacturer 5 can be sent to the system server 1 through manufacturer's 5 computing device or mobile device 4 as well. For instance, the information is automatically sent to the system server 1 whenever manufacturer's 5 mobile device 4 scans the bar code, QR code or other identification code on the medications or packaging of the medications that are to be delivered.

For convenience, the system 1 and the mobile applications may also be configured in a way that new users can join the system (e.g., register an account) and have their accounts be activated through scanning a specially designed code (e.g., bar code, QR code), a code only system administrator 2 or people authorized by system administrator have access to. Once the new user scans the specially designed code and the system verifies that the code is correct, the new user will be able to move forward with the registration and setting up their profile (e.g., name, username, last name, contact info etc.).

In yet another embodiment of the present disclosure, as shown by FIGS. 1 and 4, the system 1 is configured to works in conjunction with tamper evident bags 8 (hereafter may also be referred as "narcotic tamper evident bag"), where the system administrator 2 or authorized users 3 are required to place one count (or a specified amount) of a medication within the list into one narcotic tamper evident bag 8. For example, if there are five counts of morphine (or five units of 10 mg bottle), the system administrator 2 or authorized users 3 will need to place the five counts (or units) to five tamper evident bags 8 separately. In addition to each narcotic tamper evident bag 8 containing only one count/unit of the medication 10, the narcotic tamper evident bag 8 also contains a unique identifier 9 (e.g., bar code, QR code, RFID etc.). The tamper evident bag 8 may optionally include the name of the medication 10 in the bag 8, and any other information desired by the users such as medication's expiration date, unit number etc.

Figure 5:
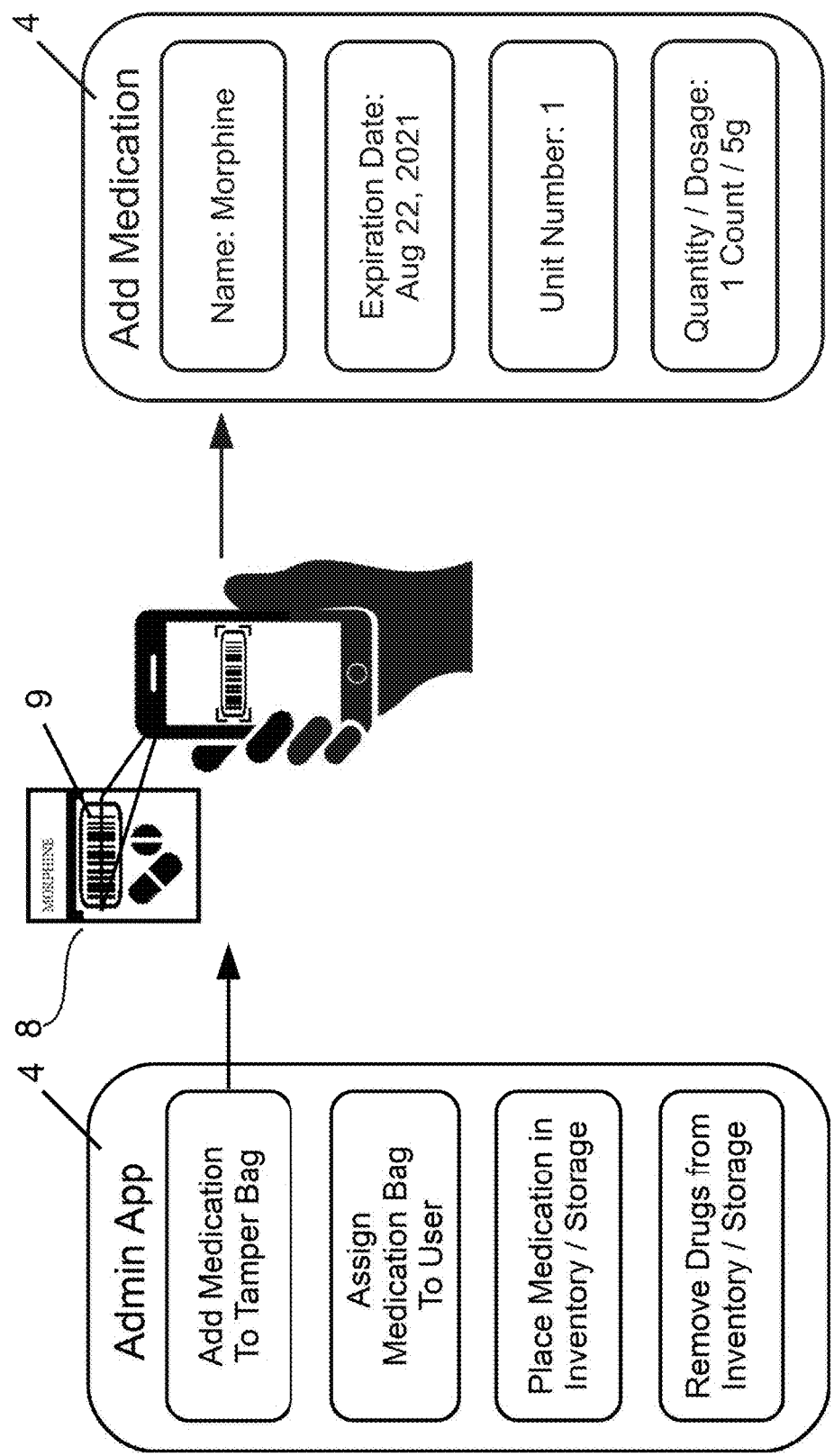
FIG. 5 is a schematic drawing according to an exemplary embodiment of the present invention.

Once a medication is put into a tamper evident bag 8, the system administrator 2 or authorized users 3 will need to associate the medication and its unique identifier 9 with the system server's 1 database. In one embodiment, as shown by FIG. 5, the system administrator 2 and/or authorized users 3 are able to do so by scanning the unique identifier 9 on the narcotic tamper evident bag 8 through the mobile application/software (e.g., Admin App) on their mobile devices or computers 4. When the unique identifier 9 is scanned, the mobile application/software will prompt the system administrator 2 or authorized users 3 to enter the medication's information such as the name, expiration date and quantify of the medication. The information is then delivered and stored in the system server's 1 database. The mobile application/software will also record and report to the system server 1 the identify of person who makes the scan and the time and date of the scan. The mobile application/software may further be configured to detect the user's location using GPS or RFID when a scan is made and record the location of the scan (e.g., at a fire station or residence etc.) as well to provide higher level of tracking.

Figure 6:
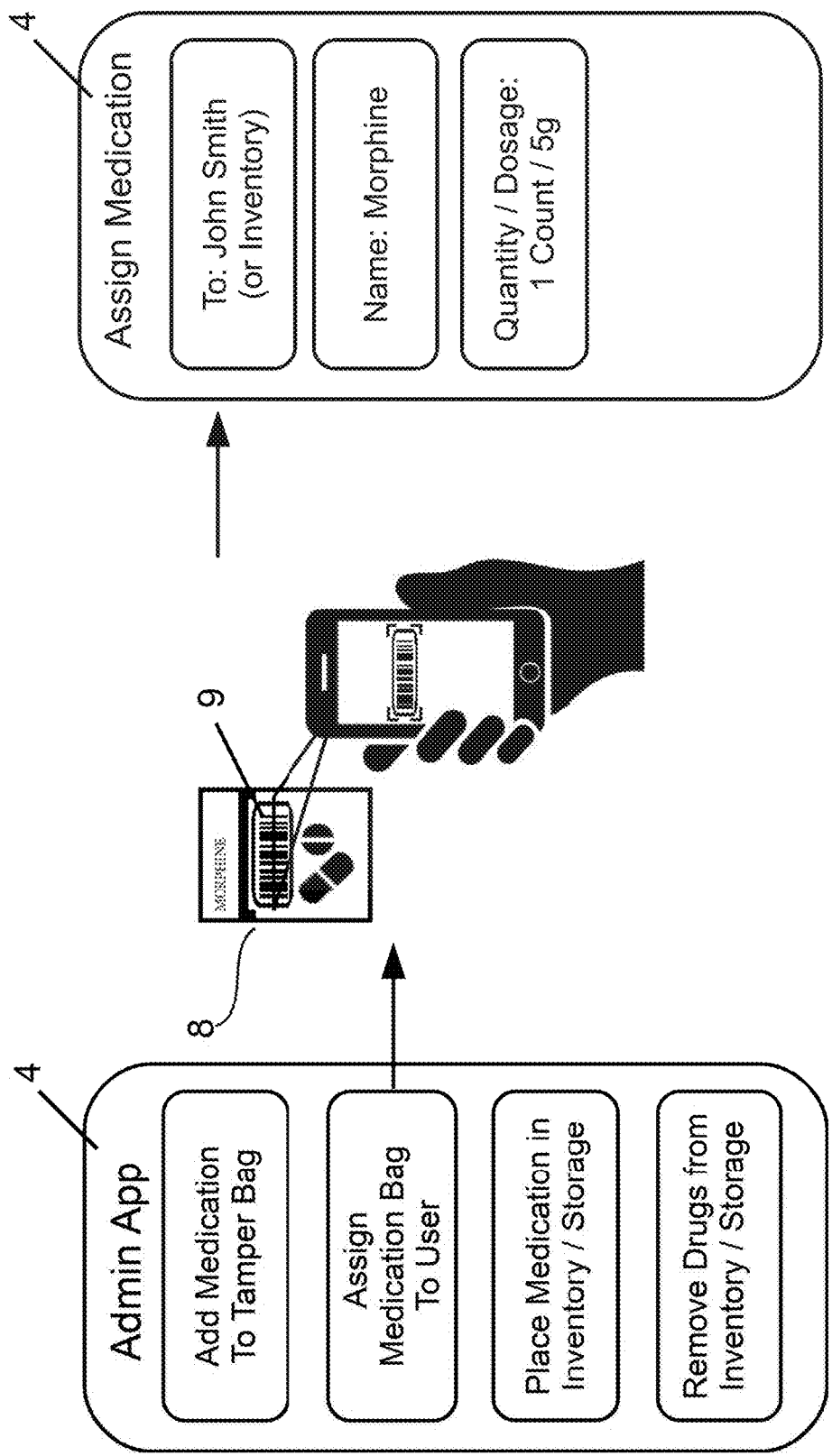
FIG. 6 is a schematic drawing according to an exemplary embodiment of the present invention.
Figure 7:
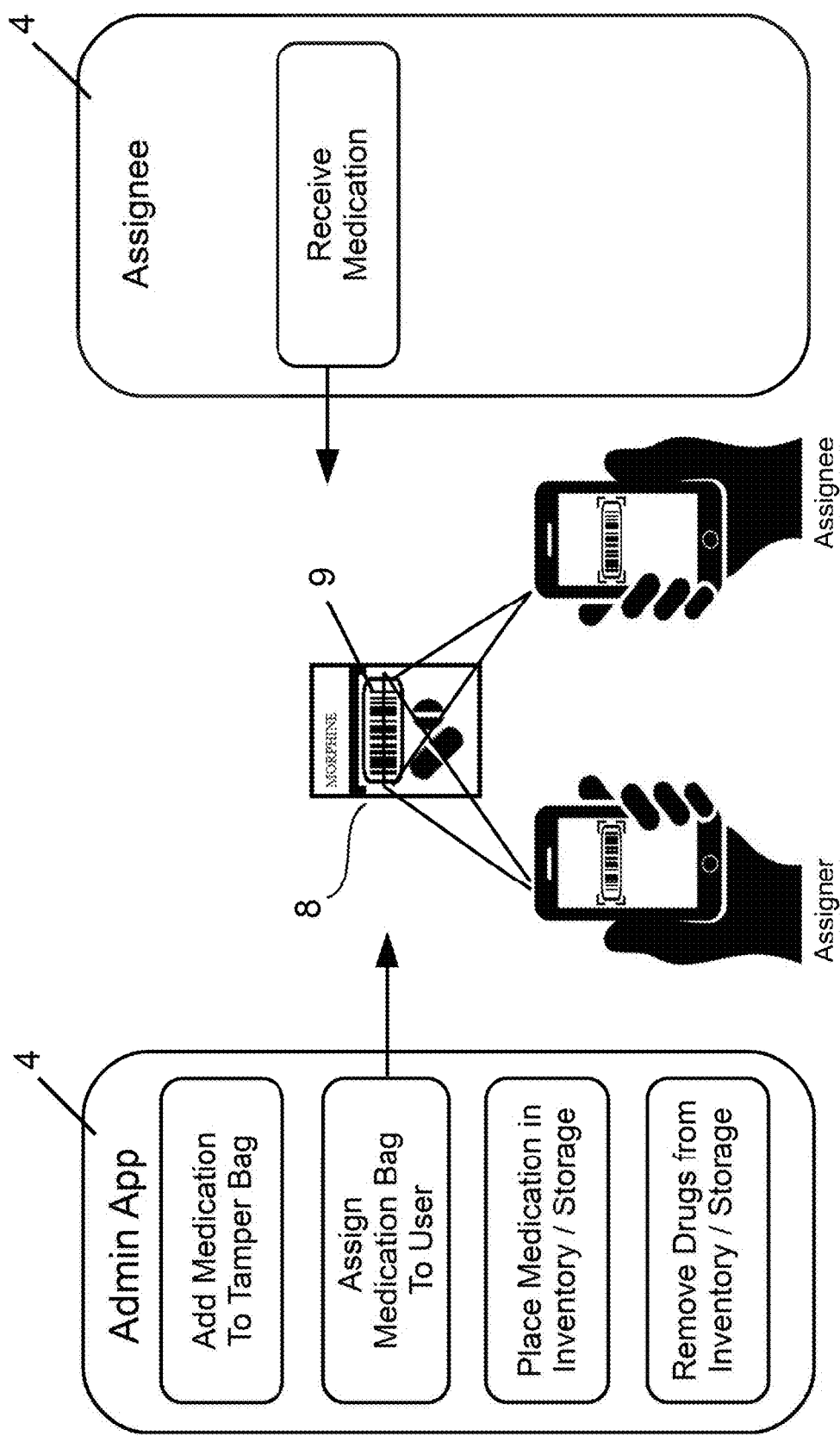
FIG. 7 is a schematic drawing according to an exemplary embodiment of the present invention.

The mobile application/software also allows the system administrator 2 and/or authorized users 3 to assign the medication in tamper evident bag 8 to other user(s), place the medication in inventory and remove the medication from inventory via similar steps. For examples, as shown by FIG. 6, the system administrator 2 and/or authorized users 3 can select the "assign medication bag to user" function on the mobile application/software and then scan the unique identifier 9. The mobile application/software will then generate a screen allowing the system administrator 2 and/or authorized users 3 to specify whom to assign the drug (or to place the drug in the inventory). Alternatively, this process can also be done by having the person assigning the medication (e.g., assigner) scans the unique identifier 9 first, and then follow by the person receiving the drug (e.g., assignee) as shown by FIG. 7. This could avoid the trouble of entering the assignee name manually and make the medication assignment quicker and more efficient. Similarly, once the assignee scans the unique identifier 9, the mobile application/software can be configured to identify additional information such as the person responsible for the scan, location of the scan (i.e., based on the phone's GPS or RFID), unit assigned and/or date and time of the scan.

Figure 8:
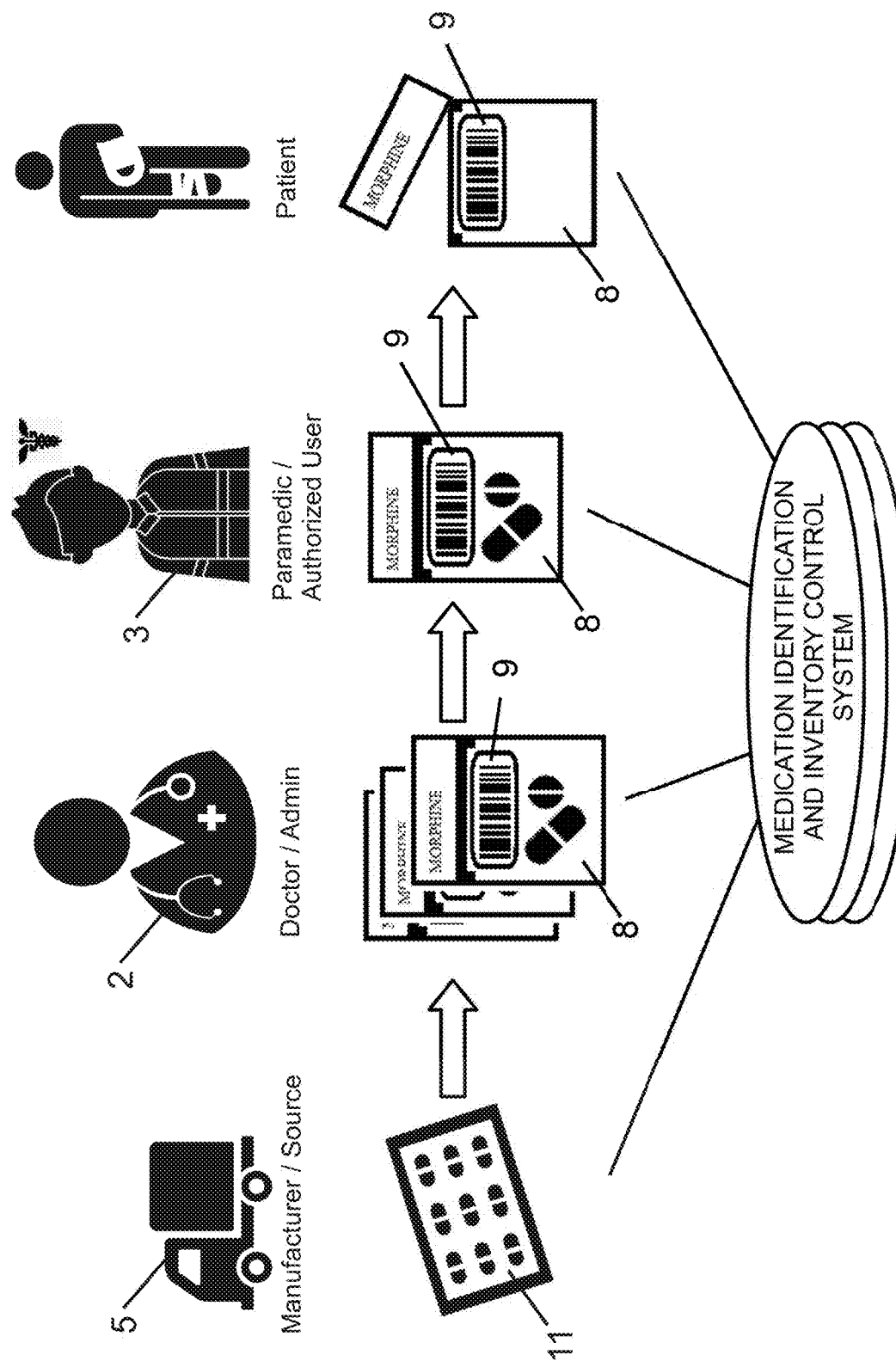
FIG. 8 is a schematic drawing according to an exemplary embodiment of the present invention.

One advantage of utilizing the narcotic tamper evident bags 8 is that they are capable of tracking and identifying each medication in the medication inventory (i.e., the list of medications) accurately as shown by FIG. 8. Currently, most medications and narcotics are purchased per box or lot 11 which contain multiple (e.g., 20 to 40) vials or ampoules per box or lot 11. Obviously, it can be inefficient and inaccurate to track medications by box 11. The disclosed narcotic tamper evident bags 8 allow users to insert one count/unit of medication per bag and each bag has its own unique identifier 9. The name of the medication and expiration date may also be displayed on the bag. The narcotic tamper evident bags 8 are tamper evident meaning anyone can identify diversion attempts by paramedics, nurses or doctors. The name of the medication and the unique barcode ID 9 on each narcotic tamper evident bag 8 give authorized users 3 or administrator 2 pinpoint accuracy when tracking the medications through the disclosed system 1. Conventional medical inventory system usually identifies the medications by lot # number and manufacturers # number only. Although some medications already have a barcode numbers attached to the label, they do not identify each medication container. Thus, by placing the medications in the narcotic tamper evident bags 8, users are capable of input as much detailed information as needed into the disclosed system 1 and optionally on the narcotic tamper evident bags 8 itself. For examples, when the unique identifier 9 was scanned by the authorized users 3 via their mobile devices or computers 4, information related to the medication in the bag can be displayed on their mobile devices or computers 4. This narcotic tamper evident bags 8 allow user to track any medication from the cradle to the grave or from the time the medication is entered into the system 1 until it was used on a patient or disposed (e.g., expired) or wasted as shown by FIG. 8. This also ensures an efficient medication accountability system due to regulations of local, state, and federal laws.

Figure 9:
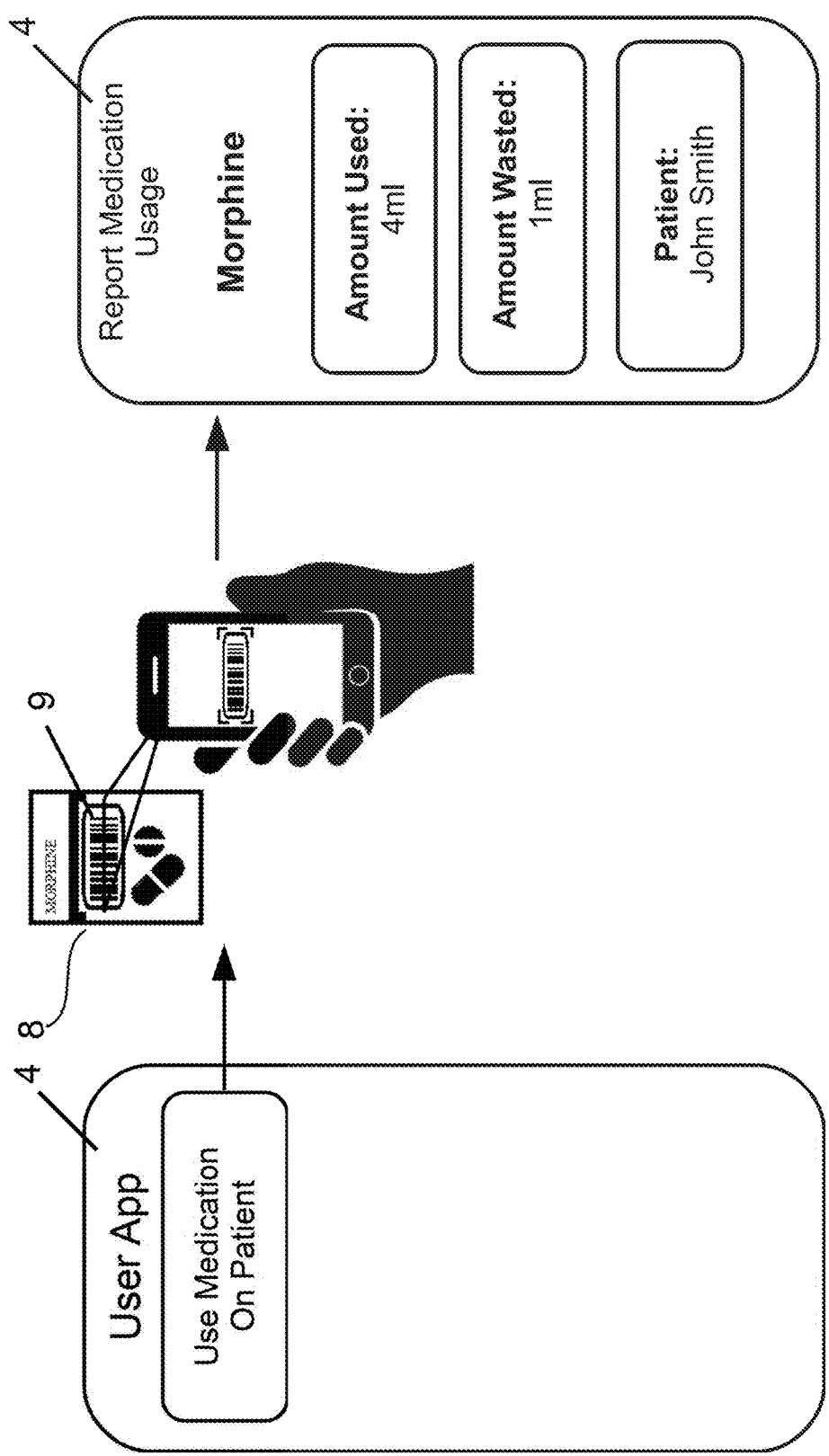
FIG. 9 is a schematic drawing according to an exemplary embodiment of the present invention.

Another advantage of using the narcotic tamper evident bag 8 is it allows the system administrator 2 and authorized users 3 to report medication usage more easily through their mobile devices 4. In one embodiment, as shown by FIG. 9, the mobile application (e.g., User App) is configured to scan (e.g., via mobile device's 4 camera) the unique identifier 9 of the narcotic tamper evident bag 8. Once the unique identifier 9 is scanned, the mobile application will automatically identify the medication in the narcotic tamper evident bag 8 and a predefined fillable form will be generated for the administrator 2 or authorized users 3 to input information relating to the medication's usage (e.g., amount of the medication used, amount of medication wasted, person who administers the medication and identity of patient/victim etc.) through the mobile application. The information relating to the medication's usage is then delivered to the system server 1 and the inventory information in the database will be updated.

Figure 10:
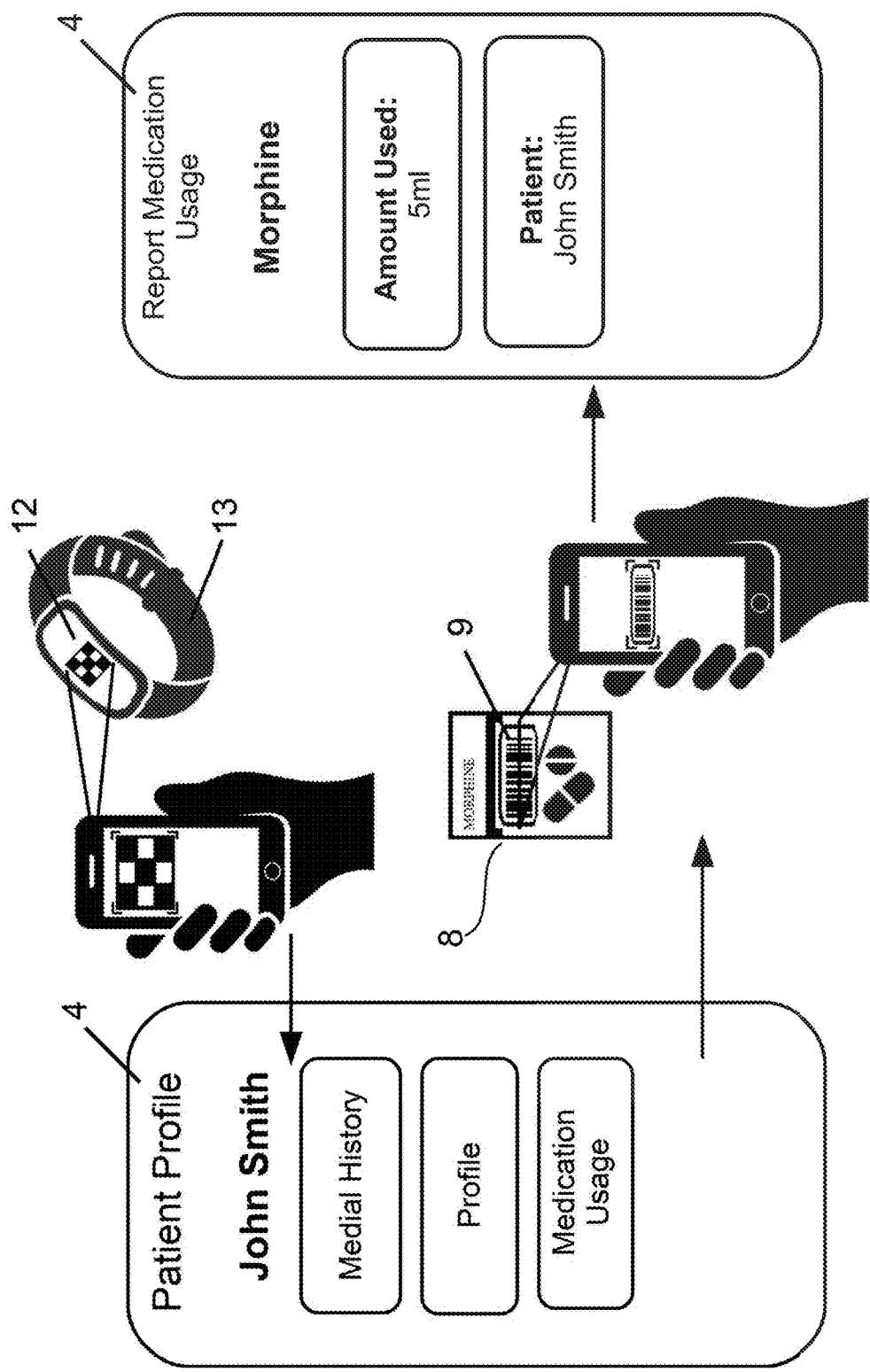
FIG. 10 is a schematic drawing according to an exemplary embodiment of the present invention.

In yet another embodiment of the present disclosure, the system administrator 2 or authorized users 3 are able to create personal profiles for their patients in the system 1. Once a patient's profile is created, the system 1 will generate a unique identification code 12 (e.g., bar code, QR code etc.) for the patient. The unique identification code 12 is intended to be printed and placed on or stayed with the patient (e.g., slap band 13, ID card etc.). As shown by FIG. 10, similar to scanning the unique barcode identifier 9 on the narcotic tamper evident bag 8, users can scan the unique identification code 12 on the patient with the mobile application and the system 1 will be able to identify and display the identity of the patient through the mobile application. Users may further be configured to have access to the patient's medical history, medication usage and other medical-related information through the scan. When the unique identification code 12 on patient is scanned in conjunction with the unique barcode identifier 9 on the narcotic tamper evident bag 8, the system 1 can be configured to assume that the medication in the narcotic tamper evident bag 8 is used on the patient and automatically records the usage information (e.g., without requiring the user to manually input the information). The usage information may also be entered manually as shown in FIG. 9.

Figure 11:
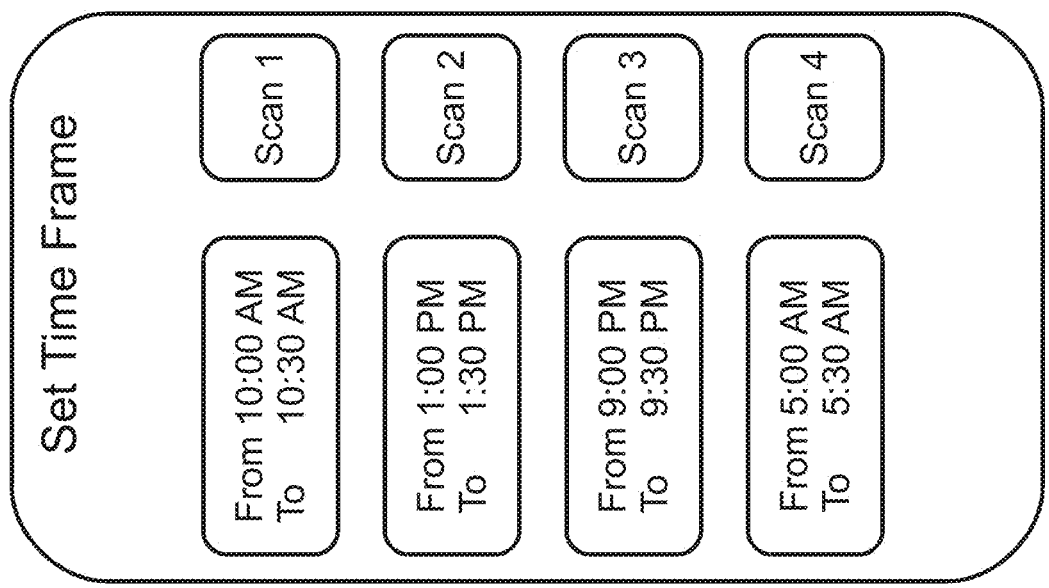
FIG. 11 is a schematic drawing according to an exemplary embodiment of the present invention.

In yet another embodiment of the present disclosure, the system 1 can be configured to request the system administrator 2 and authorized users 3 to conduct periodic inventory count (e.g., hours, every day, week, month or a customary defined duration etc.) for medications within the list. The duration for conducting periodic inventory can be set by the system administrator 2 and/or authorized users 3 as shown by FIG. 11, where an interface is generated by the mobile application for the system administrator 2 or the authorized users 3 to set time frame for medication inventory scans. The inventory count can be conducted through visual count or by scanning the unique barcode identifier 9 on all narcotic tamper evident bags 8 in the inventory. If there is a discrepancy in medication count between the record in the system server 1 and the inventory count performed by the system administrator 2 or the authorized users 3, the system 1 can be configured to notify or alert the system administrator 2 and the authorized users 3. The system 1 may also notify the system administrator 2 and/or the authorized users 3 when the required periodic inventory count was not conducted. Also, the system 1 may further be configured to notify or alert the system administrator 2, the authorized users 3 and even the medication manufacture/vendor 5 when a medication within the list of medications expires, is about to expire, depletes or is about to deplete. However, medications that are bagged and stored in a safe, cabinet, or Pyxis machine as inventory may not require periodic check to reduce users' workloads. The regular periodic check can be done by the paramedics for medications that have already been assigned to the unit and responsible personnel.

For security purposes, the system 1 can be configured to request users for identifications whenever the system administrator 2 and the authorized users 3 are trying to access the system. The user identification may comprise login/password, digital signature, biometric signature, picture identification or combination thereof. The level of identification can also be configured to be different for different medications (e.g., common medications require lower level identification while controlled medications require higher level identification etc.). Also, whenever a drug is accepted from manufacture, assigned to another user or to inventory and used on patient or wasted etc., the system 1 and its associated mobile applications/software may be configured to require the user for handwritten signature.

Figure 12:
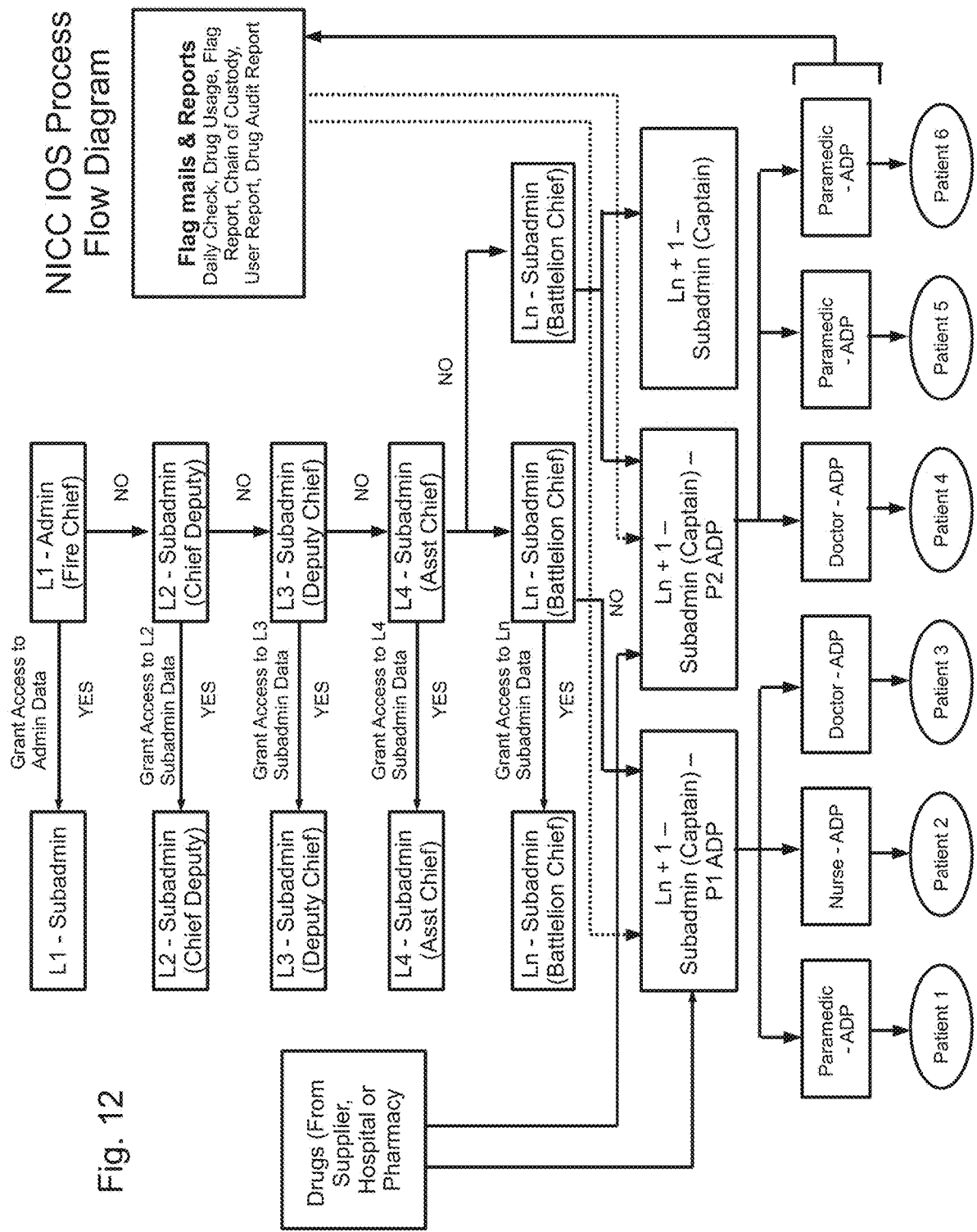
FIG. 12 is a schematic drawing according to an exemplary embodiment of the present invention.

FIG. 12 is an exemplary operating system process flow diagram for the disclosed system in accordance with one embodiment of the present disclosure. The term "NIIC" in the diagram refers to "Narcotic Identification Inventory Control" which is the system 1 disclosed above. The term ADP refers to "authorized drug personnel." L1, L2, L3 . . . , Ln, ln+1 etc. refer to level 1, level 2, level 3, level n, level n+1 respectively. From last level sub-admins, there will be drug authorized personnel—P ADP—it is from him the chain of custody of drug starts (e.g., the chain of custody starts with the ADP). The Sub-Admin could also be an ADP. For example, A Chief in a small department may not have Sub-Admin or personnel that would be assigned as an ADP. The drugs could be shipped directly to the Chief; therefore he would assign himself as the ADP to begin the life cycle of the drug in NIIC. P1ADP and P2ADP refers to 1 ADP and 2 ADP stationed at different locations. ADP's are stationed at different locations (but a location could have multiple ADPs).

In general, ADP will bring the drugs into the system (e.g., person responsible for entering the details of drugs purchased from the supplier). The ADP may further assign the drugs to units, users, Pyxis, safe and/or cabinet.

The drugs may be handled by the users listed as ADP or any other authorized users. For example, The ADP will start the drug life cycle, but once it is transferred to a User or Unit then it will be handled by the paramedic or User (this is the change in responsible personnel). Another example, a Chief in a small department may not have a Sub-Admin or personnel that would be assigned as an ADP. The drugs could be shipped directly to the Chief, therefore he would assign himself as the ADP to begin the life cycle of the drug in NIIC. Only users who have been setup as an ADP could put the drugs in the bag to start the life cycle, this includes the Chief having to setup himself up in NIIC as an ADP. The system needs to check the ADP table whenever someone accesses the "Put drug in Bag" option. If a non-authorized drug personnel tries to go into the "Put Drug in Bag" option a message should appear . . . "You are not an Authorized Drug Personnel. Contact your Administrator." Once the drug has been put in the bag it is waiting to be assigned (it is being held in inventory).

ADP may not be required to perform periodic check such as scanning the drugs in their custody because the ADP may have the drugs bagged and stored in a safe, cabinet, or Pyxis machine as inventory, waiting to be assigned to a Unit or User. The regular periodic check can be done by the paramedics for drugs that have already been assigned to the unit and responsible personnel. Drugs that are in the safe, cabinet, and Pyxis machine are waiting to be assigned.

ADP can administer drugs to patient and record the details of the patient and usage of drugs in the mobile app. For example, the way it works with LA County Fire Department is that the Division Supply Coordinator (DSC) would be the ADP person putting the drugs in the bags. The DSC's are regular paramedics who work in the stations and have been given additional responsibility to handle and control the drugs. He could be doing his work controlling the drugs and could also get a call to be on the squad to assist in an emergency to administer the drugs to a patient.

Admin & Sub admins can view all the reports (i.e., Drug audit report, daily check report, chain of custody report & User reports). Other sub admins who are not ADP will act only as watchers, monitoring the flow and usage of drugs. They cannot handle or access drugs. Only a person who can use the App (admin/sub-admin) can be an APPROVER. Otherwise they can't login into the system.

Preferably, Admins and Sub-Admins have full authority over the system (however Sub-Admin access is determined by the level he or she is granted). ADP's are a subset of the users who have been given authority to Assign Drug (put the drug in the bag). ADP's may or may not be Sub-Admins. If an ADP is a Sub-Admin, then he or she will have access to the system determined by the level they are granted. If he or she is not a subadmin, then he or she does not have access to the entire system. However, they can use the option to Assign Drug (to put the drug in a bag). If a non-authorized drug personnel tries to go into the Assign Drug option a message should appear . . . "You are not an Authorized Drug Personnel. Contact your Administrator."

Sub admins may extract NIIC reports of other divisions within the same organization depending on the situation. For example, only when logged in to the locations iPad or Desktop. When they move from one geographical location to another geographical location, then they are able to view the information that is in that area (Division or battalion). They will see the activity of the paramedics in that battalion or division.

In one configuration, flag emails (e.g., notification and alerts) are sent to the department or station email addresses, not to any person. Sub-Admin could add as many names of where they want to it to go when they setup the flag email distribution. The Sub-Admin needs to include himself on the flag email distribution as well, if he wants to receive the flag emails.

If Ln+1 subadmins are placed in different locations, 1 ADP and 2 ADP will both be responsible for adding the drugs into the system for their respective divisions. 1 sub admin will have his own user group. The ADP users under him can handle drugs which he assigned to them. 2 sub admin will have his own user group. However, he can only assign drugs which was entered by him into the system and cannot assign drugs entered by Primary 1 sub admin.

Authorized Drug Personnel instructions—Authorized Drug Personnel (only certain users are authorized to put drugs into the bags to begin the tracking). Only Admin or Sub-Admins could authorize personnel to put drugs into bags. Admin or Sub-Admin must also authorize themselves to be "Authorized Drug Personnel" if they need to put drugs in the bags. Only Authorized Drug Personnel could assign a drug to a bag or to a unit. If a non-authorized user tries to go into the Assign Drug option a message should appear . . . "You are not an Authorized Drug Personnel." If someone is being setup as an Authorized Drug Personnel and their name is not in the system as a User, then they must be setup as a User first. Show message . . . "This person is not found in User list. Must setup as User first."

Admin/Sub-Admin Business Rules—there is only one Admin (it's the person who bought the system). A Sub-Admin is optional (if Admin does not create a Sub-Admin then Admin will do all of the setups). Admin starts off the Sub-Admins: (if a Sub-Admin is needed, they have to be setup through the Assign Sub-Admin Selection):

Exemplary Show questions on the screen:
a. Grant access at your level? Y/N
(Y for your level, N for their level)
Note: If "Y" then Sub-Admin can view at that level, if "N" the Sub-Admin can view only at the next lower level (see diagram)
b. What type of access?: View/Update
(View only or Can make updates)
c. What is their access status?: On/Off
(On can access system or Off cannot access system)
d. Can they create other Sub-Admins?: Y/N
(Y can setup other people or No cannot setup other people)
Note: If "Y" they can access the Create Sub-Admin option to create more Sub-Admins, if "N" they are locked out of the Create Sub-Admin option when going into the selection. Show message "Not authorized to create Sub-Admins."

Shift Change and Change in Personnel will transfer responsibility for any position when necessary (Battalion Chief, Captain, Paramedic, etc.). This will occur when one Sub-Admin logs out and the other logs in. No special selection is needed for this.

As long as the person is in the Sub-Admin table the system will allow them access to another Battalion Division or Fire Station. Note if any user picks up the Admin app and scans their QR code or tries to login, if they are not in the Sub-Admin table they will be blocked. Show message "Not authorized to access NIIC Admin."

Any Sub-Admin at a lower level could be turned off at any time by a higher level Sub-Admin for that area (this is the Access status On/Off). NIIC Admin will be access through Departmental mobile devices (iPads and Desktops). Personnel hands over devices at shift changes; it stays logged in.

The system could have anywhere from 1000 to 1500 Sub-Admins at one time. Secretaries could even be setup as Sub-Admins, but may not be able to create Sub-Admins, the options selected through the Sub-Admin setup will determine access to grant to secretaries or anyone else setup as Sub-Admins.

In yet another embodiment of the present disclosure, a method of providing medication identification and inventory control is disclosed. The method comprises: receiving registration information from a system administrator and authorized users and store the registration information in a database of a system server; requesting the system administrator or authorized users, via their mobile devices or computers, to specify a list of medications that are to be tracked and their current inventory status; storing the list of medications and their current inventory status in the database; when a medication within the list is delivered from a manufacture or a source and received by the system administrator or by the authorized users or at a place specified by the system administrator or authorized users, requesting the system administrator or the authorized users to confirm quantity of the medication received matches the quantify of the medication delivered from the manufacturer or the source and the medication's expiring date, and send the confirmation and the expiring date to the system server to update the current inventory status for the medication in the database; placing one count or a specified amount of each medication within the list into a tamper evident bag, where each tamper evident bag has a unique identifier that identifies at least the name of medication in the tamper evident bag upon scanning by a mobile device or computer, wherein information related to medication in each tamper evident bag and its associated unique identifier is stored in the database and the system server tracks number of counts of each medication available in inventory; when a medication within the list needs to be used or wasted, the system administrator or authorized users are required to open the tamper evident bag containing the medication and scan the unique identifier on the tamper evident bag with their mobile devices or computers, wherein a predefined fillable form will be displayed on their mobile devices or computers' screen for inputting information relating to the medication's usage, and the inputted information is delivered to the system server and the current inventory status of the medication in the database is updated; and generating medication inventory report periodically or upon request by the system administrator or authorized users for medications within the list of medications, wherein the medication inventory report comprises at least medications' usage, breakage, waste and expiration.

The information relating to the medication's usage includes at least amount of the medication used or amount of medication wasted.

In yet another exemplary aspect, the disclosed method may further comprise requesting the system administrator or authorized users to conduct periodic inventory count for medications in the list of medications through their mobile devices or computers, wherein the periodic inventory count is conducted by scanning the unique identifier on all tamper evident bags in the inventory. When a mismatch in periodic inventory count is detected, system administrator and/or authorized users would be alerted.

In yet another exemplary aspect, the disclosed method may further comprise notifying or alerting the system administrator or the authorized users when a medication within the list of medications expires, is about to expire, depletes or is about to deplete.

In yet another exemplary aspect, the disclosed method may further comprise receiving information relating to a patient or a victim from the system administrator or authorized users; creating a profile for the patient or the victim and store the profile in the database; generating a profile code for the patient or the victim, wherein the profile code is printed and placed on the patient or the victim, and the profile code is scanned before any medication within the list of medication is administered to the patient or the victim to make server keeps a record of medication usage for each patient or victim.

In yet another embodiment of the present disclosure, a non-transitory computer readable medium storing computer executable instruction for medication identification and inventory control is disclosed. This including instructions for: receiving registration information from a system administrator and authorized users; requesting the system administrator or authorized users, via their mobile devices or computers, to enter a list of medications that are to be tracked and medications' information, wherein medications' information include at least name and current inventory count of each medication entered; receiving and storing the list of medications and medications' information in a database; receiving a delivery notification from the system administrator or authorized users when a medication within the list of medication is delivered from a manufacture or a source and received by the system administrator or by the authorized users or at a place specified by the system administrator or authorized users; wherein the delivery notification includes at least system administrator or authorized users' confirmation confirming quantity of the medication received matches the quantify of the medication delivered; updating the inventory count of the medication in the database based on the delivery notification; receiving medication usage via the system administrator or authorized users' mobile devices or computers when a medication within the list of medication is used or wasted and update the medication's information in the database; prompting the system administrator or authorized users to place one count of each medication within the list of medications into a tamper evident bag, where each tamper evident bag has a unique identifier that identifies at least the name of the medication in the tamper evident bag upon scanning by a mobile device or computer; notifying the system administrator or authorized users to conduct periodic inventory count for medications in the list of medications through their mobile devices or computers, wherein the periodic inventory count is conducted by scanning the unique identifier on all tamper evident bags in the inventory; receiving the periodic inventory count from the system administrator or authorized users via their mobile devices or computers and verify whether the periodic inventory count matches the inventory count in the database, and send alert to the system administrator or authorized users when a mismatch is detected; and generating and deliver a medication inventory report periodically or upon request by the system administrator or authorized users for medications within the list of medications, wherein the medication inventory report comprises at least medications' usage, breakage, waste and expiration.

In various aspects, the systems and methods described herein may be implemented in hardware, software, firmware, or any combination thereof. If implemented in software, the methods may be stored as one or more instructions or code on a non-transitory computer-readable medium. Computer-readable medium includes data storage. By way of example, and not limitation, such computer-readable medium can comprise RAM, ROM, EEPROM, CD-ROM, Flash memory or other types of electric, magnetic, or optical storage medium, or any other medium that can be used to carry or store desired program code in the form of instructions or data structures and that can be accessed by a processor of a general purpose computer.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should also be noted that when the term "a", "an", etc. is used, it is to be interpreted as "at least one" throughout the application, drawings, and claims. Furthermore, it is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of the skilled in the relevant art(s). Moreover, it is not intended for any term in the specification or claims to be ascribed an uncommon or special meaning unless explicitly set forth as such.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

A portion of the disclosure of this patent document including any priority documents contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

What is claimed is:

1. A system for medication identification and inventory control, the system comprising: a server having a hardware processor configured to:
   receive registration information from a system administrator and authorized users;
   request the system administrator or authorized users, via their mobile devices or computers, to enter a list of medications that are to be tracked and information about the medications, wherein the medications' information include at least name and current inventory count of each medication entered;
   receive and store the list of medications and medications' information in a database;
   receive a delivery notification from the system administrator or authorized users when a medication within the list of medication is delivered from a manufacture or a source and received by the system administrator or by the authorized users or at a place specified by the system administrator or authorized users, wherein the delivery notification includes at least system administrator or authorized users' confirmation confirming a quantity of the medication received matches a quantity of the medication delivered and an expiration date of the medication;
   update the inventory count and expiration date of the medication in the database based on the delivery notification;
   receive medication usage via the system administrator or authorized users' mobile devices or computers when a medication within the list of medication is used or wasted and update the medication's information in the database;
   prompt the system administrator or authorized users to place one count of each medication within the list of medications into a tamper evident bag, wherein each tamper evident bag has a unique identifier that identifies at least the name of the medication in the tamper evident bag upon scanning by one of the mobile devices or computers, wherein information related to medication in each tamper evident bag and its associated unique identifier is stored in the database and the server tracks a number of counts of each medication available in inventory;
   notify the system administrator or authorized users to conduct periodic inventory count for medications in the list of medications through one of the mobile devices or computers, wherein the periodic inventory count is conducted by scanning the unique identifier on all the tamper evident bags in the inventory;
   receive the periodic inventory count from the system administrator or authorized users via one of the mobile devices or computers and verify whether the periodic inventory count matches the inventory count in the database, and send alert to the system administrator or authorized users when a mismatch is detected;
   receive information relating to a patient or a victim from the system administrator or authorized users;
   create a profile for the patient or the victim and store in the database;
   generate a profile code for the patient or the victim, wherein the profile code is printed and placed on the patient or the victim, and the profile code is scanned before any medication within the list of medication is administered to the patient or the victim to make the server keep a record of medication usage for each patient or victim; and
   generate and deliver a medication inventory report periodically or upon request by the system administrator or authorized users for medications within the list of medications, wherein the medication inventory report comprises at least medications' usage, breakage, waste and expiration.

2. The system of claim 1, wherein information relating to the medication delivered from the manufacture or the source is automatically transmitted to the server whenever the manufacturer or the source's mobile device scans a bar code, QR code or other identification code on the medication or packaging of the medication before or during the delivery.

3. The system of claim 1, wherein the tamper evident bag is a narcotic tamper evident bag.

4. The system of claim 1, wherein the unique identifier is a bar code or a QR code.

5. The system of claim 1, wherein when the unique identifier is scanned via a camera of the mobile device or computer, a predefined fillable form will be displayed on a screen of the mobile device or computer for inputting information relating to the medication's usage, and the information is delivered to the server.

6. The system of claim 5, wherein the inputted information relating to the medication's usage includes at least amount of the medication used and amount of medication wasted.

7. The system of claim 1, wherein the periodic inventory count is conducted by scanning the unique identifiers on the tamper evident bags in the inventory.

8. The system of claim 1 further comprises: notify or alert the system administrator or the authorized users when a medication within the list of medications expires, is about to expire, depletes or is about to deplete.

9. The system of claim 1, wherein the system administrator or authorized users are personnel from a fire station, a hospital, a pharmacy or an emergency medical service (EMS).

10. A method of providing medication identification and inventory control, the method comprising:
  receiving, by a processor, registration information from a system administrator and authorized users and store the registration information in a database of a system server;
  requesting, by the processor, the system administrator or authorized users, via their mobile devices or computers, to specify a list of medications that are to be tracked and their current inventory status;
  storing, by the processor, the list of medications and their current inventory status in the database, wherein when a medication within the list is delivered from a manufacture or a source and received by the system administrator or by the authorized users or at a place specified by the system administrator or authorized users, the processor requests the system administrator or the authorized users to confirm a quantity of the medication received matches a quantity of the medication delivered from the manufacturer or the source and a medication's expiring date, and send the confirmation and the expiring date to the system server to update the current inventory status for the medication in the database;
  receiving, by the processor and after scanning by one of the mobile devices or computers, a unique identifier of a tamper evident bag upon placing one count or a specified amount of each medication within the list into the tamper evident bag, wherein each tamper evident bag has a unique identifier that identifies at least the name of medication in the tamper evident bag, wherein information related to medication in each tamper evident bag and its associated unique identifier is stored in the database and the system server tracks a number of counts of each medication available in inventory;
  receiving, by the processor and after scanning by one of the mobile devices or computers, the unique identifier on the tamper evident bag when a medication within the list needs to be used or wasted, wherein the system administrator or authorized users are required to open the tamper evident bag containing the medication, and wherein, upon the scanning, a predefined fillable form is displayed on a screen of the one of the mobile devices or computers for inputting information relating to the medication's usage, and the inputted information is delivered to the system server and the current inventory status of the medication in the database is updated;
  receiving, by the processor, information relating to a patient or a victim from the system administrator or authorized users;
  creating, by the processor, a profile for the patient or the victim and store in the database;
  generate, by the processor, a profile code for the patient or the victim, wherein the profile code is printed and placed on the patient or the victim, and the profile code is scanned before any medication within the list of medication is administered to the patient or the victim to make the server keep a record of medication usage for each patient or victim; and
  generating, by the processor, medication inventory report periodically or upon request by the system administrator or authorized users for medications within the list of medications, wherein the medication inventory report comprises at least medications' usage, breakage, waste and expiration.

11. The method of claim 10, wherein the inputted information relating to the medication's usage includes at least amount of the medication used or amount of medication wasted.

12. The method of claim 10 further comprises: requesting the system administrator or authorized users to conduct periodic inventory count for medications in the list of medications through their mobile devices or computers, wherein the periodic inventory count is conducted by scanning the unique identifier on all tamper evident bags in the inventory.

13. The method of claim 12 further comprises alerting the system administrator or authorized users when a mismatch in periodic inventory count is detected.

14. The method of claim 10, further comprises: notifying or alerting the system administrator or the authorized users when a medication within the list of medications expires, is about to expire, depletes or is about to deplete.

15. A non-transitory computer readable medium storing computer executable instruction for medication identification and inventory control, including instructions for:
  receiving registration information from a system administrator and authorized users;
  requesting the system administrator or authorized users, via their mobile devices or computers, to enter a list of medications that are to be tracked and information about the medications, wherein the medications' information include at least name and current inventory count of each medication entered;
  receiving and storing the list of medications and medications' information in a database;
  receiving a delivery notification from the system administrator or authorized users when a medication within the list of medication is delivered from a manufacture or a source and received by the system administrator or by the authorized users or at a place specified by the system administrator or authorized users, wherein the delivery notification includes at least system administrator or authorized users' confirmation confirming quantity of the medication received matches the quantify of the medication delivered;
  updating the inventory count of the medication in the database based on the delivery notification;
  receiving medication usage via the system administrator or authorized users' mobile devices or computers when a medication within the list of medication is used or wasted and update the medication's information in the database;
  prompting the system administrator or authorized users to place one count of each medication within the list of medications into a tamper evident bag, wherein each tamper evident bag has a unique identifier that identifies at least the name of the medication in the tamper evident bag upon scanning by one of the mobile devices or computers, wherein information related to medication in each tamper evident bar and its associated unique identifier is stored in the database and the server tracks a number of counts of each medication available in inventory;

notifying the system administrator or authorized users to conduct periodic inventory count for medications in the list of medications through their mobile devices or computers, wherein the periodic inventory count is conducted by scanning the unique identifier on all tamper evident bags in the inventory;

receiving the periodic inventory count from the system administrator or authorized users via their mobile devices or computers and verify whether the periodic inventory count matches the inventory count in the database, and send alert to the system administrator or authorized users when a mismatch is detected;

receiving information relating to a patient or a victim from the system administrator or authorized users;

creating a profile for the patient or the victim and store in the database;

generating a profile code for the patient or the victim, wherein the profile code is printed and placed on the patient or the victim, and the profile code is scanned before any medication within the list of medication is administered to the patient or the victim to make the server keep a record of medication usage for each patient or victim; and generating and deliver a medication inventory report periodically or upon request by the system administrator or authorized users for medications within the list of medications, wherein the medication inventory report comprises at least medications' usage, breakage, waste and expiration.

16. The non-transitory computer readable medium of claim 15, wherein when the unique identifier is scanned via a camera of the mobile device or computer, a predefined fillable form will be displayed on a screen of the mobile device or computer for inputting information relating to the medication's usage, and the information is delivered to the server.

17. The non-transitory computer readable medium of claim 15 further comprises: notifying or alerting the system administrator or the authorized users when a medication within the list of medications expires, is about to expire, depletes or is about to deplete.

* * * * *